US012694950B2

(12) United States Patent
Bridges et al.

(10) Patent No.: US 12,694,950 B2
(45) Date of Patent: Jul. 28, 2026

(54) COMPARATIVELY-REFINED POLYGENIC RISK SCORE GENERATION MACHINE LEARNING FRAMEWORKS

(71) Applicant: Optum Services (Ireland) Limited, Dublin (IE)

(72) Inventors: Michael Bridges, Dublin (IE); Paul J. Godden, London (GB)

(73) Assignee: Optum Services (Ireland) Limited, Dublin (IE)

( * ) Notice: Subject to any disclaimer, the term of this patent is extended or adjusted under 35 U.S.C. 154(b) by 1010 days.

(21) Appl. No.: 17/804,416

(22) Filed: May 27, 2022

(65) Prior Publication Data

US 2022/0383982 A1 Dec. 1, 2022

Related U.S. Application Data

(60) Provisional application No. 63/202,148, filed on May 28, 2021.

(51) Int. Cl.
G16B 40/00 (2019.01)
G16B 10/00 (2019.01)
G16B 20/20 (2019.01)
(52) U.S. Cl.
CPC ............. G16B 40/00 (2019.02); G16B 10/00 (2019.02); G16B 20/20 (2019.02)
(58) Field of Classification Search
CPC ........ G16B 40/00; G16B 20/00; G16B 20/20; G16B 20/40; G16B 10/00; G16B 40/20; G16H 50/70; G16H 50/30
See application file for complete search history.

(56) References Cited

U.S. PATENT DOCUMENTS 9,598,733 B2      3/2017  Gharvari et al.
11,985,930 B2 *   5/2024  Cooper ................... G16B 5/00
(Continued)

FOREIGN PATENT DOCUMENTS

WO      2006/099142 A2      9/2006
WO      2020/172432 A1      8/2020
(Continued)

OTHER PUBLICATIONS

Skilling, John. "Nested sampling for general Bayesian computation." (2006): 833-859. (Year: 2006).*
(Continued)

*Primary Examiner* — Jesse P Frumkin
(74) *Attorney, Agent, or Firm* — ALSTON & BIRD LLP

(57) ABSTRACT

Various embodiments of the present invention describe techniques for generating a polygenic risk score generation machine learning framework that integrates an optimal genetic variant refinement model without requiring brute-force traversal of potential parameter spaces defined by various distinct genetic variant sets. In response, various embodiments of the present invention use holistic Bayesian sampling routines to efficiently generate Bayesian evidence numerical estimates for various genetic variant refinement models and select an optimal genetic variant refinement model accordingly. This enables enhancing the accuracy of polygenic risk score generation machine learning frameworks without resorting to computationally resource-intensive traversals of potential parameter spaces defined by various distinct genetic variant sets. In doing so, various embodiments of the present invention enhance the computational efficiency of generating a polygenic risk score generation machine learning framework that integrates an optimal genetic variant refinement model in contrast to
(Continued)

computationally-inefficient techniques that require brute-force traversal of potential parameter spaces.

20 Claims, 7 Drawing Sheets

(56) References Cited

U.S. PATENT DOCUMENTS

| | | | | |
|---|---|---|---|---|
| 2014/0032122 A1* | 1/2014 | Bader | ................... | G16B 20/00 |
| | | | | 702/19 |
| 2019/0345566 A1* | 11/2019 | Khera | ................... | G16H 50/20 |
| 2020/0118647 A1* | 4/2020 | Zhang | ................... | G16B 30/00 |
| 2021/0113536 A1 | 4/2021 | Natarajan et al. | | |
| 2021/0118571 A1 | 4/2021 | Hsu et al. | | |
| 2023/0154618 A1* | 5/2023 | Enderling | ............. | G16H 20/00 |
| | | | | 705/3 |
| 2023/0391875 A1* | 12/2023 | Chandler | .............. | A61K 45/06 |
| 2024/0105280 A1* | 3/2024 | Moore | ................... | G16B 40/00 |
| 2025/0266129 A1* | 8/2025 | Polcari | ................... | G16B 40/20 |

FOREIGN PATENT DOCUMENTS

| | | | | |
|---|---|---|---|---|
| WO | 2020/264466 A1 | 12/2020 | | |
| WO | WO-2021011990 A1 * | 1/2021 | ............. | G16B 20/40 |
| WO | 2021/038234 A1 | 3/2021 | | |
| WO | WO-2022084554 A1 * | 4/2022 | ............. | G06F 17/18 |

OTHER PUBLICATIONS

Johnson, Rob, Paul Kirk, and Michael PH Stumpf. "SYSBIONS: nested sampling for systems biology." Bioinformatics 31.4 (2014): 604-605. (Year: 2014).*

Thijssen, Bram, et al. "BCM: toolkit for Bayesian analysis of computational models using samplers." BMC Systems Biology 10.1 (2016): 100. (Year: 2016).*

Kochen, Michael Allen. Mechanistic Hypothesis Exploration of Signaling Network Processes via Bayesian Inference Methods. Diss. Vanderbilt University, 2020. (Year: 2020).*

Mikelson, Jan, and Mustafa Khammash. "Likelihood-free nested sampling for parameter inference of biochemical reaction networks." PLoS computational biology 16.10 (2020): e1008264. (Year: 2020).*

Speagle, Joshua S. "dynesty: a dynamic nested sampling package for estimating Bayesian posteriors and evidences." Monthly Notices of the Royal Astronomical Society 493.3 (2020): 3132-3158. (Year: 2020).*

Pasetto, Stefano, Robert A. Gatenby, and Heiko Enderling. "Bayesian framework to augment tumor board decision making." JCO Clinical Cancer Informatics 5 (2021): 508-517. (Year: 2021).*

Song, Shuang, Lin Hou, and Jun S. Liu. "A data-adaptive Bayesian regression approach for polygenic risk prediction." Bioinformatics 38.7 (2022): 1938-1946. (Year: 2022).*

Gabbutt, Calum, et al. "Reconstruction of Contemporary Human Stem Cell Dynamics with Oscillatory Molecular Clocks." bioRxiv (2021): Mar. 2021. (Year: 2021).*

Choi, Shing Wan et al. "A Guide to Performing Polygenic Risk Score Analyses," Nature Protocols, vol. 15, No. 9, pp. 2759-2772, Sep. 2020 (ePub: Jul. 24, 2020), DOI: 10.1038/s41596-020-0353-1.

Feroz, F. et al. "Multinest: An Efficient and Robust Bayesian Inference Tool for Cosmology and Particle Physics," Monthly Notices of the Royal Astronomical Society, vol. 398, Issue 4, pp. 1601-1614, Oct. 2009 (ePub: Sep. 17, 2009), DOI: 10.1111/j.1365-2966.2009.14548.x.

Handley, W.J. et al. "Polychord: Next-Generation Nested Sampling," Monthly Notices of the Royal Astronomical Society, vol. 453, Issue 4, pp. 4384-4398, Nov. 11, 2015, (ePub: Sep. 16, 2015), DOI: 10.1093/mnras/stv1911.

Higson, Edward et al. "Dynamic Nested Sampling: An Improved Algorithm for Parameter Estimation and Evidence Calculation," Statistics and Computing, vol. 29, Issue 5, pp. 891-913, Sep. 2019, (ePub: Dec. 3, 2018), DOI: 10.1007/s11222-018-9844-0.

Mavaddat, Nasim et al. "Polygenic Risk Scores for Prediction of Breast Cancer and Breast Cancer Subtypes," The American Journal of Human Genetics, vol. 104, Issue 1, pp. 21-34, Jan. 3, 2019, DOI: 10.1016/j.ajhg.2018.11.002.

Skilling, John. "Nested Sampling for General Bayesian Computation," Bayesian Analysis vol. 1, No. 4, pp. 833-860, Dec. 2006.

So, Hon-Cheong et al. "Improving Polygenic Risk Prediction From Summary Statistics by an Empirical Bayes Approach, " Scientific Reports, vol. 7, No. 41262, pp. 1-11, Feb. 1, 2017, DOI: 10.1038/srep41262.

Thibodeau, Eric L. "Child Maltreatment, Adaptive Functioning, and Polygenic Risk: A Structural Equation Mixture Model," Developyment and Psychopathology, vol. 31, No. 2, pp. 433-456, May 2019, DOI: 10.1017/S095479419000014.

Vilhjalmsson, Bjarni J. et al. "Modeling Linkage Disequilibrium Increases Accuracy of Polygenic Risk Scores," The American Journal of Human Genetics, vol. 97, No. 4, Oct. 1, 2015, pp. 576-592, DOI: 10.1016/j.ajhg.2015.09.001.

International Search Report and Written Opinion for International Application No. PCT/US2022/031352; dated Aug. 11, 2022, (12 pages), European Patent Office, Rijswijk, Netherlands.

* cited by examiner

External Computing Entities 102

Predictive Data Analysis Computing Entity 106

Storage Subsystem 108

Predictive Data Analysis System 101

400

Identify genome-wide association studies (GWAS) data
401

Generate refined GWAS data
402

Generate a comparatively-refined polygenic risk score
generation machine learning framework
403

Identify genetic variant refinement models
501

Generate per-model parameter numerical estimate sets and Bayesian evidence numerical estimates
502

Generate a comparatively-refined polygenic risk score generation machine learning framework
503

Perform testing/validation operations
504

Identify genome-wide association studies (GWAS) data for a particular individual
601

Generate a polygenic risk score
602

Perform prediction-based actions
603

COMPARATIVELY-REFINED POLYGENIC RISK SCORE GENERATION MACHINE LEARNING FRAMEWORKS

CROSS-REFERENCES TO RELATED APPLICATION(S)

The present patent application claims priority to the U.S. Provisional Patent Application No. 63/202,148, filed on May 28, 2021, which is incorporated by reference herein in its entirety.

BACKGROUND

Various embodiments of the present invention address technical challenges related to performing health-related predictive data analysis. Various embodiments of the present invention address the shortcomings of existing health-related predictive data analysis systems and disclose various techniques for efficiently and reliably performing health-related predictive data analysis.

BRIEF SUMMARY

In general, various embodiments of the present invention provide methods, apparatus, systems, computing devices, computing entities, and/or the like for performing health-related predictive data analysis. Certain embodiments of the present invention utilize systems, methods, and computer program products that perform health-related predictive data analysis by generating a comparatively-refined polygenic risk score generation machine learning framework that comprises an optimal genetic variant refinement model, where the optimal genetic variant refinement model is selected from a plurality of defined genetic variant refinement models based at least in part on Bayesian evidence numerical estimates for the plurality of defined genetic variant refinement models. Once generated, the comparatively-refined polygenic risk score generation machine learning framework can be used to generate a polygenic risk score for a particular individual with respect to a target phenotype (e.g., a target medical condition).

In accordance with one aspect, a method is provided. In one embodiment, the method comprises: (i) identifying a comparatively-refined polygenic risk score generation machine learning framework, wherein: (a) the comparatively-refined polygenic risk score generation machine learning framework comprises an optimal genetic variant refinement model that is selected from a plurality of defined genetic variant refinement models, (b) each defined genetic variant refinement model: (i) is associated with: (a) a distinct per-model genetic variant set of a group of genetic variants, and (b) a per-model parameter set comprising a per-model effect weight parameter set for the distinct per-model genetic variant set that is associated with the defined genetic variant refinement model, and (ii) is configured to generate a per-model polygenic risk score based at least in part on a per-model input feature vector corresponding to the distinct per-model genetic variant set for the defined genetic variant refinement model and the per-model parameter set for the defined genetic variant refinement model, and (c) generating the optimal genetic variant refinement model comprises: (i) for each defined genetic variant refinement model, sampling from a per-model posterior probability distribution for the defined genetic variant refinement model given target genome-wide association data for the target phenotype and by using a holistic Bayesian sampling routine that is configured to generate: (a) a per-model parameter numerical estimate set for the per-model parameter set that is associated with the defined genetic variant refinement model, and (b) a Bayesian evidence numerical estimate for the defined genetic variant refinement model, and (ii) selecting the optimal genetic variant refinement model as the defined genetic variant refinement model with an optimal Bayesian evidence numerical estimate as generated by the holistic Bayesian sampling routine, (ii) generating a polygenic risk score based at least in part on the per-model polygenic risk score for the optimal genetic variant refinement model; and (iii) performing one or more prediction-based actions based at least in part on the polygenic risk score.

In accordance with another aspect, a computer program product is provided. The computer program product may comprise at least one computer-readable storage medium having computer-readable program code portions stored therein, the computer-readable program code portions comprising executable portions configured to: (i) identify a comparatively-refined polygenic risk score generation machine learning framework, wherein: (a) the comparatively-refined polygenic risk score generation machine learning framework comprises an optimal genetic variant refinement model that is selected from a plurality of defined genetic variant refinement models, (b) each defined genetic variant refinement model: (i) is associated with: (a) a distinct per-model genetic variant set of a group of genetic variants, and (b) a per-model parameter set comprising a per-model effect weight parameter set for the distinct per-model genetic variant set that is associated with the defined genetic variant refinement model, and (ii) is configured to generate a per-model polygenic risk score based at least in part on a per-model input feature vector corresponding to the distinct per-model genetic variant set for the defined genetic variant refinement model and the per-model parameter set for the defined genetic variant refinement model, and (c) generating the optimal genetic variant refinement model comprises: (i) for each defined genetic variant refinement model, sampling from a per-model posterior probability distribution for the defined genetic variant refinement model given target genome-wide association data for the target phenotype and by using a holistic Bayesian sampling routine that is configured to generate: (a) a per-model parameter numerical estimate set for the per-model parameter set that is associated with the defined genetic variant refinement model, and (b) a Bayesian evidence numerical estimate for the defined genetic variant refinement model, and (ii) selecting the optimal genetic variant refinement model as the defined genetic variant refinement model with an optimal Bayesian evidence numerical estimate as generated by the holistic Bayesian sampling routine, (ii) generate a polygenic risk score based at least in part on the per-model polygenic risk score for the optimal genetic variant refinement model; and (iii) perform one or more prediction-based actions based at least in part on the polygenic risk score.

In accordance with yet another aspect, an apparatus comprising at least one processor and at least one memory including computer program code is provided. In one embodiment, the at least one memory and the computer program code may be configured to, with the processor, cause the apparatus to: (i) identify a comparatively-refined polygenic risk score generation machine learning framework, wherein: (a) the comparatively-refined polygenic risk score generation machine learning framework comprises an optimal genetic variant refinement model that is selected from a plurality of defined genetic variant refinement models, (b) each defined genetic variant refinement model: (i) is associated with: (a) a distinct per-model genetic variant set of a group of genetic variants, and (b) a per-model parameter set comprising a per-model effect weight parameter set for the distinct per-model genetic variant set that is associated with the defined genetic variant refinement model, and (ii) is configured to generate a per-model polygenic risk score based at least in part on a per-model input feature vector corresponding to the distinct per-model genetic variant set for the defined genetic variant refinement model and the per-model parameter set for the defined genetic variant refinement model, and (c) generating the optimal genetic variant refinement model comprises: (i) for each defined genetic variant refinement model, sampling from a per-model posterior probability distribution for the defined genetic variant refinement model given target genome-wide association data for the target phenotype and by using a holistic Bayesian sampling routine that is configured to generate: (a) a per-model parameter numerical estimate set for the per-model parameter set that is associated with the defined genetic variant refinement model, and (b) a Bayesian evidence numerical estimate for the defined genetic variant refinement model, and (ii) selecting the optimal genetic variant refinement model as the defined genetic variant refinement model with an optimal Bayesian evidence numerical estimate as generated by the holistic Bayesian sampling routine, (ii) generate a polygenic risk score based at least in part on the per-model polygenic risk score for the optimal genetic variant refinement model; and (iii) perform one or more prediction-based actions based at least in part on the polygenic risk score.

BRIEF DESCRIPTION OF THE DRAWINGS

Figure 1:

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
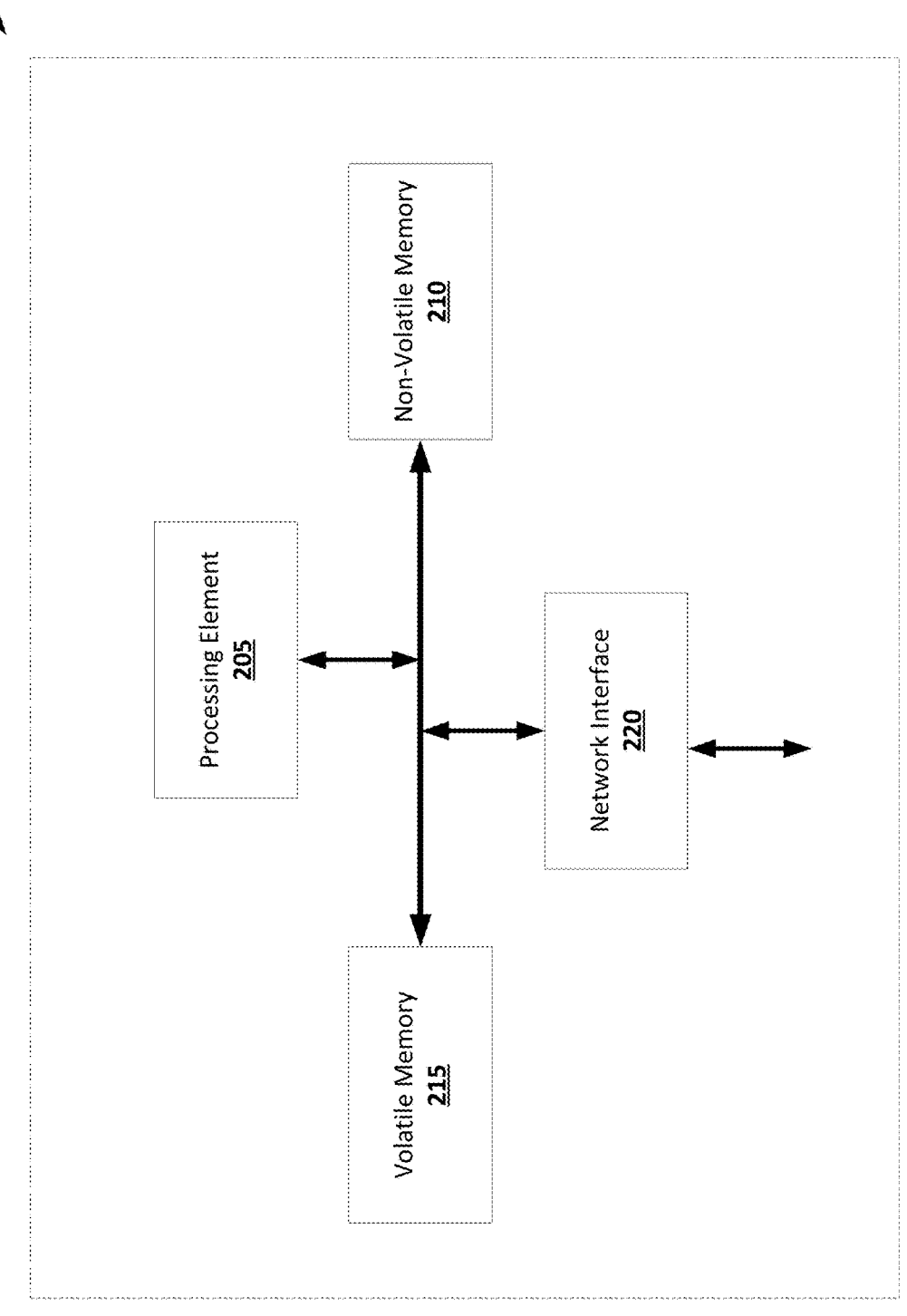

FIG. 2 provides an example predictive data analysis computing entity in accordance with some embodiments discussed herein.

Figure 3:
Figure 3:
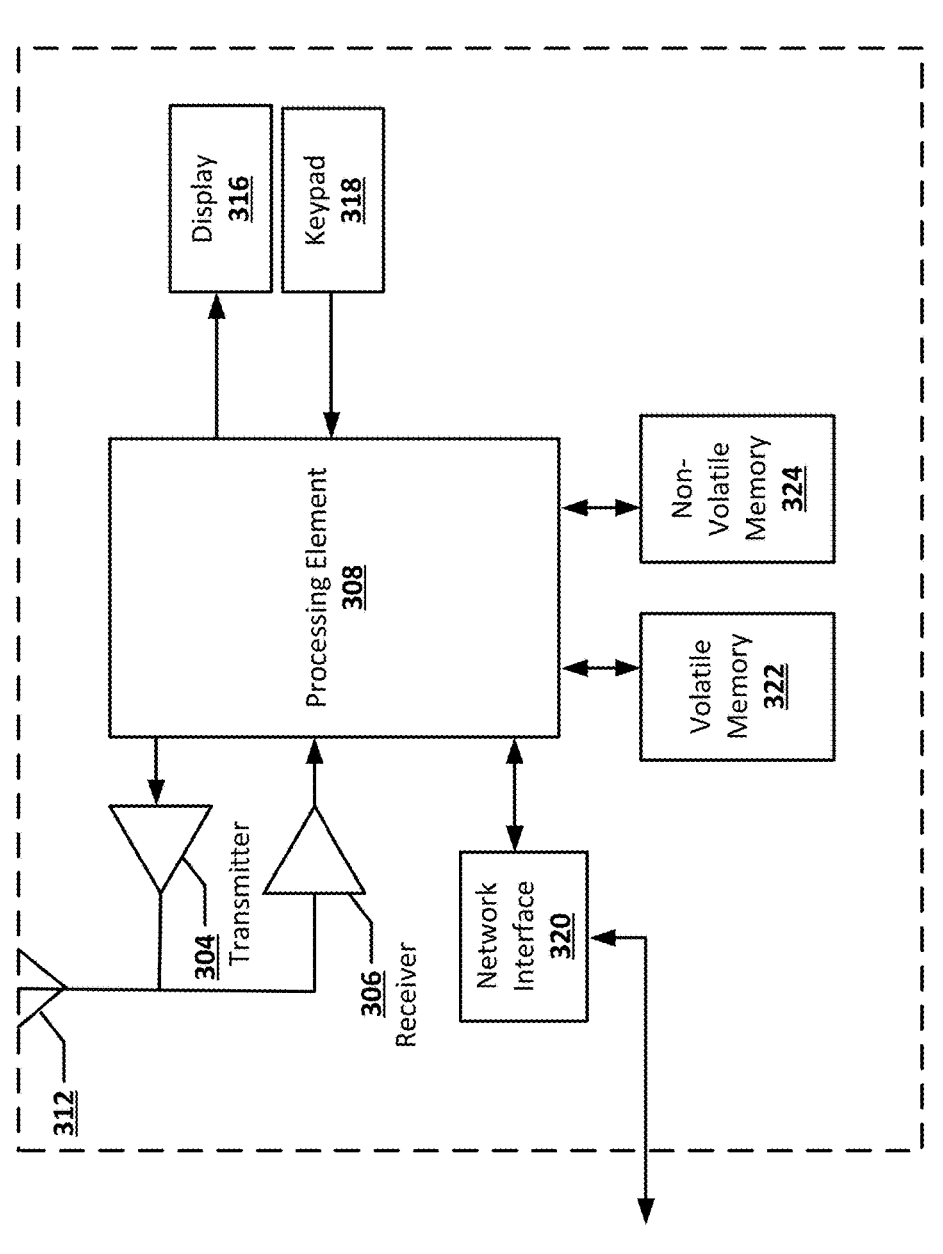

FIG. 3 provides an example external computing entity in accordance with some embodiments discussed herein.

Figure 4:
Figure 4:
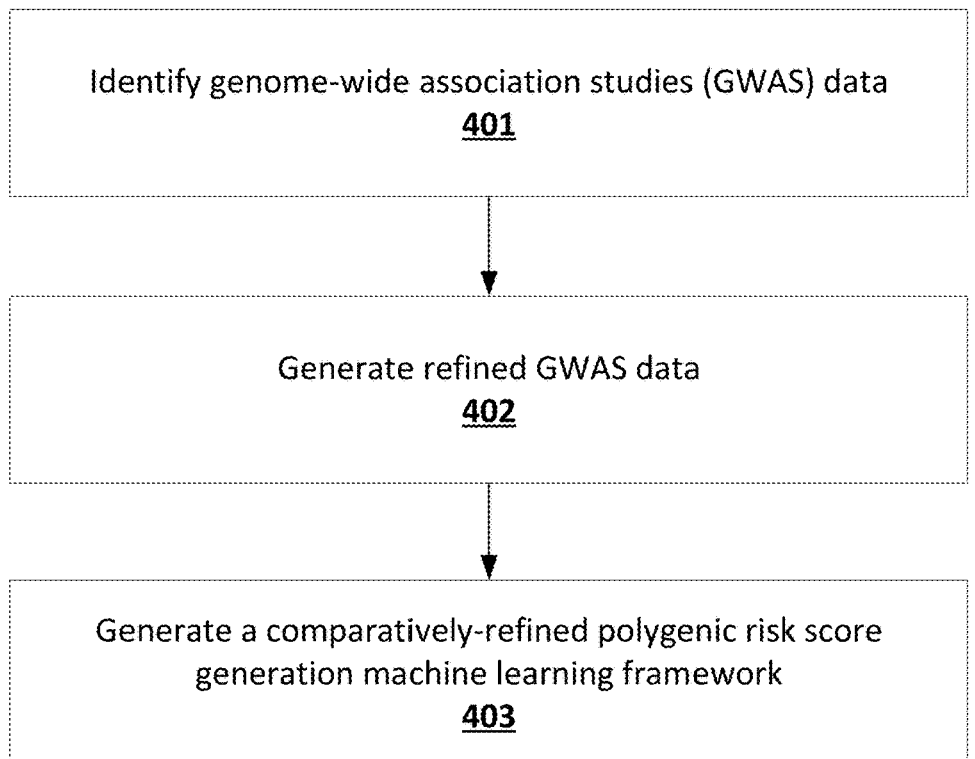

FIG. 4 is a flowchart diagram of an example process for generating a comparatively-refined polygenic risk score generation machine learning framework in accordance with some embodiments discussed herein.

Figure 5:
Figure 5:
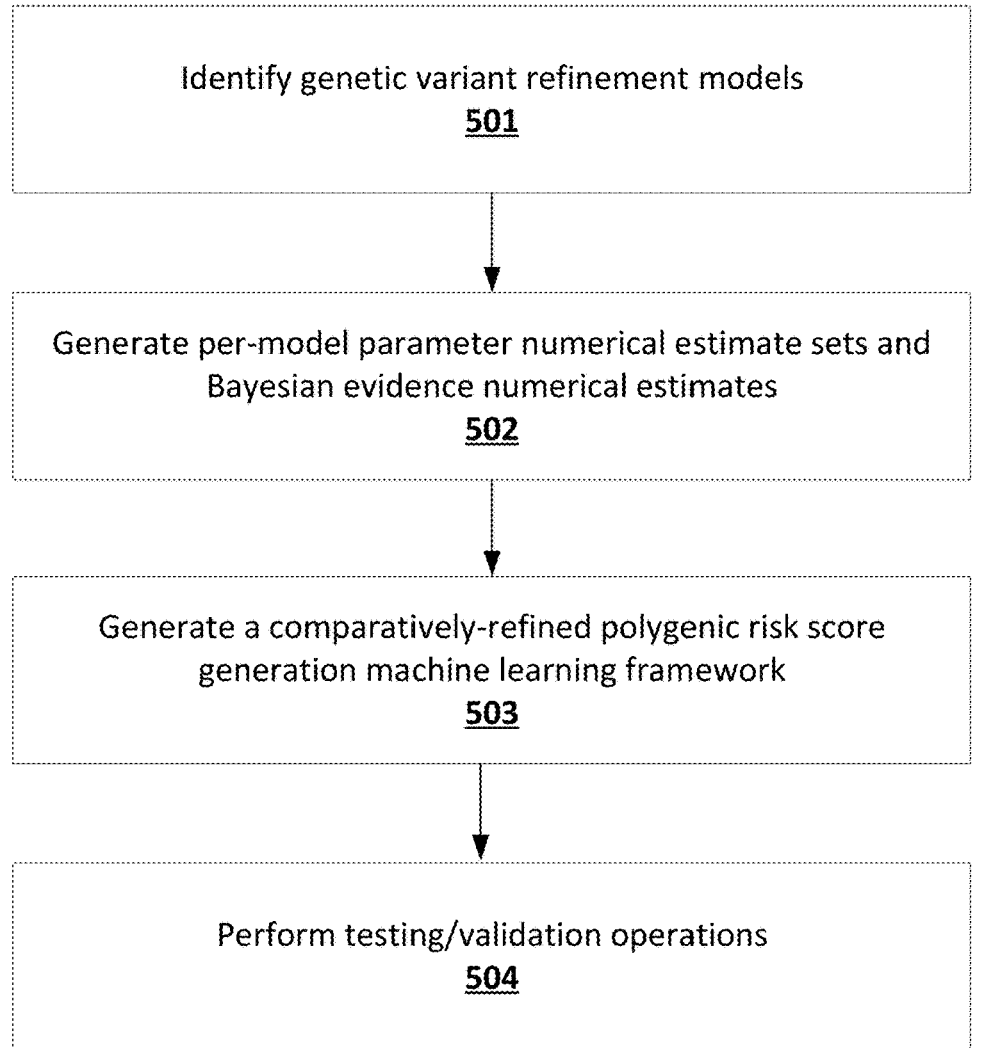

FIG. 5 is a flowchart diagram of an example process for generating a comparatively-refined polygenic risk score generation machine learning framework based at least in part on the refined genome-wide association studies (GWAS) data in accordance with some embodiments discussed herein.

Figure 6:
Figure 6:
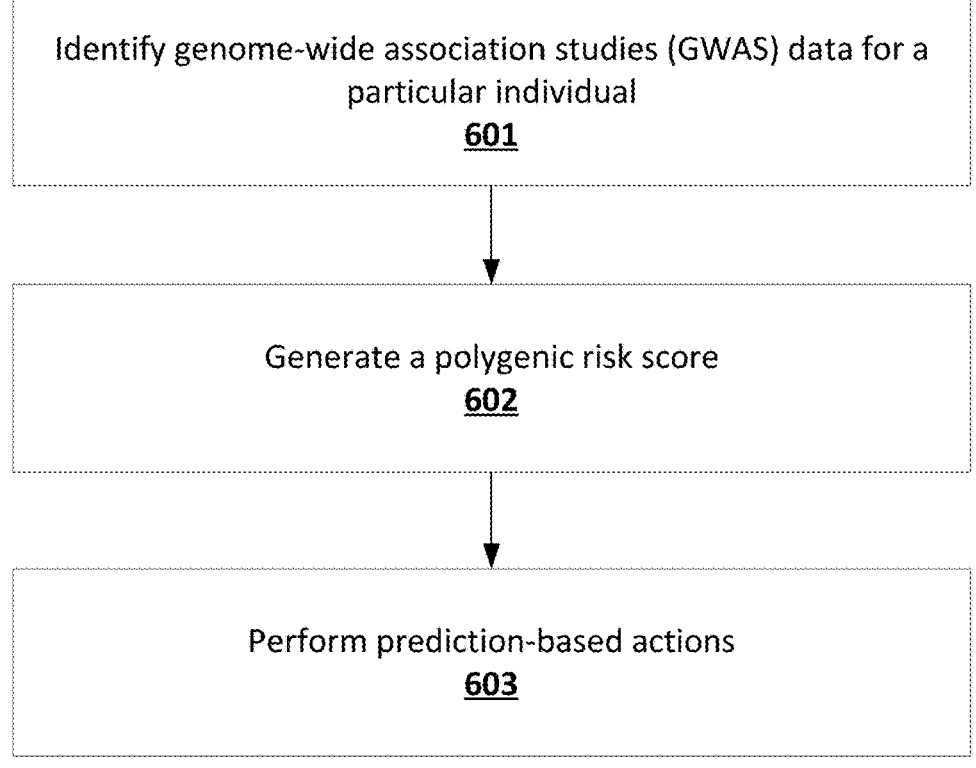

FIG. 6 is a flowchart diagram of an example process for generating a polygenic risk score for a particular individual with respect to a target phenotype in accordance with some embodiments discussed herein.

Figure 7:

FIG. 7 provides an operational example of a predictive output user interface in accordance with some embodiments discussed herein.

DETAILED DESCRIPTION

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. Overview and Technical Advantages

Various embodiments of the present invention describe techniques for generating a polygenic risk score generation machine learning framework that integrates an optimal genetic variant refinement model without requiring brute-force traversal of potential parameter spaces defined by various distinct genetic variant sets. In some embodiments, when a polygenic risk score for a particular individual with respect to a target phenotype is generated in accordance with the operations of the equation $$PRS = \sum_{j=1}^{N_L} X_j \beta_j$$

as described below, the genetic variant set used to generate the noted polygenic risk score generation model may be any subset of an overall set of genetic variants (e.g., the set of all single-nucleotide polymorphisms (SNPs) that are present in human genome). Selecting an optimal genetic variant set for a particular polygenic risk score generation model that is configured to generate polygenic risk scores for a particular target phenotype is a computationally challenging task. A naïve solution to this problem is to generate the optimal genetic variant set to include each genetic variant whose correlation score (e.g., p value) with respect to the target phenotype as observed by the refined GWAS data satisfies (e.g., exceeds) a defined correlation score. However, this naïve approach fails to integrate interactions between variable-size groupings of genetic variants. In contrast, various embodiments of the present invention use holistic Bayesian sampling routines to efficiently generate Bayesian evidence numerical estimates for various genetic variant refinement models and select an optimal genetic variant refinement model accordingly. This enables enhancing the accuracy of polygenic risk score generation machine learning frameworks without resorting to computationally resource-intensive traversals of potential parameter spaces defined by various distinct genetic variant sets. In doing so, various embodiments of the present invention enhance the computational efficiency of generating a polygenic risk score generation machine learning framework that integrates an optimal genetic variant refinement model in contrast to computationally-inefficient techniques that require brute-force traversal of potential parameter spaces defined by various distinct genetic variant sets.

Moreover, various embodiments of the present invention make important technical contributions to improving resource-usage efficiency of post-prediction systems by using polygenic-risk-score-based predictions to set the number of allowed computing entities used by the noted post-prediction systems. For example, in some embodiments, a predictive data analysis computing entity determines D inferred classifications for D individuals based at least in part on the D polygenic risk scores for the D individuals. Then, the count of individuals that are associated with an affirmative inferred classification, along with a resource utilization ratio for each individual, can be used to predict a predicted number of computing entities needed to perform post-prediction processing operations (e.g., automated investigation operations) with respect to the D individuals. For example, in some embodiments, the number of computing entities needed to perform post-prediction processing operations (e.g., automated investigation operations) with respect to D individuals can be determined based at least in part on the output of the equation:

$$R = \operatorname{ceil}\left(\sum_{k}^{k=K} ur_k\right),$$

where R is the predicted number of computing entities needed to perform post-prediction processing operations with respect to the D individual, cello) is a ceiling function that returns the closest integer that is greater than or equal to the value provided as the input parameter of the ceiling function, k is an index variable that iterates over K individuals among the D polygenic risk scores that are associated with affirmative classifications, and $ur_k$ is the estimated resource utilization ratio for a kth individual that may be determined based at least in part on a count of utterances/tokens/words in the kth individual. In some embodiments, once R is generated, the predictive data analysis computing entity can use R to perform operational load balancing for a server system that is configured to perform post-prediction processing operations (e.g., automated investigation operations) with respect to D individuals. This may be done by allocating computing entities to the post-prediction processing operations if the number of currently-allocated computing entities is below R, and deallocating currently-allocated computing entities if the number of currently-allocated computing entities is above R.

In some embodiments, a polygenic risk score (PRS) is a single number summarisation of the estimated statistical effect of a set of genetic variants with a patients phenotype. A PRS for an individual is in some embodiments constructed by first identifying a set of genetic variants, often single nucleotide polymorphisms (SNPs), and defining a set of weightings associated with each in a linear sum by using the equation: $PRS=X_1\beta_1+X_2\beta_2+X_3\beta_3+ \ldots +X_N\beta_N$ In the above-noted equation, X is a matrix representing the presence of, and β represents the weight associated with, a given genetic variant (often a SNP). The choice of which variants to include in the model and their relative weights are in some embodiments at the core of PRS estimation. Most analyses define the PRS based at least in part on a predetermined set of SNPs known to have association with a disease through studies. An optimisation is then performed to estimate the relative importance of each SNP to the correlation and these become the estimated weightings or β's.

In some embodiments, a key question relates to how many SNPs to include. A proposed system uses a rigorous method using Bayesian statistics to both optimise the calculation of the values of the weights and also crucially to allow different PRS models to be compared quantitatively using the Bayesian evidence statistic. This metric is a single number that encapsulates the model fit to the data but crucially one that penalises models which are overly complex, thus naturally incorporating Occam's Razor (simpler explanations are more likely to be correct). As a result a 10 SNP PRS model for Breast Cancer could have the highest evidence even though a 100 SNP model might produce a slightly better fit to the data.

Accordingly, various embodiments of the present invention use a method of Bayesian numerical sampling called nested sampling to efficiently and optimally estimate the most likely weights for each SNP following summary statistics and simultaneously compute the Bayesian evidence for this model. This process can be repeated for any choice of PRS model and thus multiple PRSs can be directly and quantitatively compared.

II. Definitions of Certain Terms

The term "defined genetic variant refinement model" may refer to a data object that is configured to describe at least one of: (i) a distinct per-model genetic variant set, and (ii) a per-model parameter set comprising a per-model effect weight parameter set for the distinct per-model genetic variant set that is associated with the defined genetic variant refinement model. In some embodiments, a polygenic risk score is generated as a weighted sum of effect weights for genetic variants (e.g., single-nucleotide polymorphisms (SNPs)) in a particular genetic variant set, for example in accordance with the operations of the equation $$PRS = \sum_{j=1}^{N_L} X_j \beta_j,$$

where: (i) PRS is a polygenic risk score for a particular individual with respect to a target phenotype, (ii) each $x_a$ is an indicator that describes whether the genetic variant a in a set of genetic variants $N_L$ is present/observed in the refined GWAS data for the particular individual, (iii) each $\beta_a$ is a weighted effect weight parameter for the genetic variant a in the set of genetic variants $N_L$ with respect to the target phenotype, and (iv) $N_L$ is the set of genetic variants (e.g., SNPs) that are determined/computed to be related to the target phenotype. In some embodiments, a defined genetic variant refinement model provides a recommended genetic variant set (i.e., a defined $N_L$) for the target phenotype. In some embodiments, once a defined genetic variant refinement model is identified, a proposed system may sample from a posterior distribution for the defined genetic variant refinement model to generate a Bayesian evidence numerical estimate for the defined genetic variant refinement model, and then defined genetic variant refinement model having an optimal (e.g., a maximum) Bayesian evidence numerical estimate may be selected as the optimal genetic variant refinement model.

The term "per-model genetic variant set" may refer to a data object that is configured to describe a selected set of genetic variants (e.g., SNPs) as defined by a genetic variant refinement model. In some embodiments, given V set of genetic variants, M distinct subsets of the V set of genetic variants are generated (e.g., based at least in part on subject matter expert data), and each distinct subset is adopted as the per-model genetic variant set for a respective genetic variant refinement model of M genetic variant refinement models.

The term "per-model parameter set" may refer to a data object that is configured to describe a set of parameters for a posterior probability distribution for the per-model genetic variant set of a corresponding genetic variant refinement model. As described above, in some embodiments, a genetic variant refinement model is associated with a distinct genetic variant set. In some embodiments, given a particular genetic variant set, a posterior probability distribution P r(β, n_p, S, . . . , ID) can be generated, where: (i) {β, n_p, S, . . . } is the set of parameters of the posterior probability distribution including β, which is the set of weighted effect weight parameters for each genetic in the defined the particular genetic variant set, and (ii) D is the refined GWAS data. In some embodiments, the combination of a genetic variant set and a set of parameters for a posterior probability distribution for the genetic variant set is referred to herein as a defined genetic variant refinement model. Accordingly, in some embodiments, given M distinct genetic variant sets, M genetic variant refinement models are defined, with each genetic variant refinement model being associated with a respective genetic variant set and describing both the respective genetic variant set and the parameters for the posterior probability distribution that is associated with the respective genetic variant set.

The term "holistic Bayesian sampling routine" may refer to a data object that is configured to describe parameters, hyper-parameters, and/or defined operations of a computer-implemented routine that is configured to sample from a posterior probability distribution in a manner that traverses a parameter space by varying more than parameter dimension at each sampling iteration. Holistic Bayesian sampling routines can be contrasted with non-holistic Bayesian sampling routines such as Gibbs in which the parameter space is traversed by varying only one parameter dimension at each sampling iteration. Because of their holistic traversal approach, Holistic Bayesian sampling routines are able to capture predictive correlations between parameters more effectively. Examples of holistic Bayesian sampling routines include nested sampling routines and hybrid sampling routines that comprise a nested sampling sub-routine and a dynamic nested sampling sub-routine. In some embodiments, when the holistic Bayesian sampling routine comprises a nested sampling sub-routine and a dynamic nested sampling sub-routine, for a particular defined genetic variant refinement model, the nested sampling sub-routine is configured to generate a first Bayesian evidence numerical estimate for the particular defined genetic variant refinement model as generated by the nested sampling sub-routine, while the dynamic nested sampling sub-routine is configured to generate a second Bayesian evidence numerical estimate for the particular defined genetic variant refinement model as generated by the dynamic nested sampling sub-routine. In some embodiments, the Bayesian evidence numerical estimate for the particular defined genetic variant refinement model is generated based at least in part on a cross-estimate weighted combination of the first Bayesian evidence numerical estimate and the second Bayesian evidence numerical estimate, where the cross-estimate weighted combination may be generated based at least in part on (e.g., by adding) the product of applying a weight for the nested sampling routine (e.g., a weight of 0.5) to the first Bayesian evidence numerical estimate and the product of applying a weight for the dynamic nested sampling routine (e.g., a weight of 0.5) to the second Bayesian evidence numerical estimate. In some of the noted embodiments, the weight of the nested sampling routine is generated based at least in part on a historical model performance quality weight for the nested sampling routine that describes a computed accuracy of per-model polygenic risk scores generated in accordance with optimal genetic variant refinement models selected in accordance with Bayesian evidence numerical estimates that are generated using the nested sampling routine relative to ground-truth polygenic risk scores. In some of the noted embodiments, the weight of the dynamic nested sampling routine is generated based at least in part on a historical model performance quality weight for the dynamic nested sampling routine that describes a computed accuracy of per-model polygenic risk scores generated in accordance with optimal genetic variant refinement models selected in accordance with Bayesian evidence numerical estimates that are generated using the nested sampling routine relative to ground-truth polygenic risk scores.

The term "comparatively-refined polygenic risk score generation machine learning framework" may refer to a data object that is configured to describe parameters, hyper-parameters, and/or defined operations of one or more machine learning models, where the one or more machine learning models are configured to generate a polygenic risk score for a particular individual with respect to a target phenotype based at least in part on GWAS data (e.g., refined GWAS data) associated with the particular individual. In some embodiments, the comparatively-refined polygenic risk score generation machine learning framework is configured to perform operations of one or more polygenic risk score generation machine learning models, where each polygenic risk score generation machine learning model is configured to generate a polygenic risk score for a particular individual with respect to a target phenotype in accordance with the operations of the equation $$PRS = \sum_{j=1}^{N_L} X_j \beta_j,$$

where: (i) PRS is the polygenic risk score for the particular individual with respect to the target phenotype, (ii) each $x_a$ is an indicator that describes whether the genetic variant a in a set of genetic variants $N_L$ is present/observed in the refined GWAS data for the particular individual, (iii) each $\beta_a$ is a weighted effect weight parameter for the genetic variant a in the set of genetic variants $N_L$ with respect to the target phenotype, and (iv) $N_L$ is the set of genetic variants (e.g., SNPs) that are determined/computed to be related to the target phenotype. In some embodiments, the comparatively-refined polygenic risk score generation machine learning framework is configured to perform operations of a single polygenic risk score generation machine learning model, where the $N_L$ for the single polygenic risk score generation machine learning model is the distinct genetic variant set for the optimal genetic variant refinement model, and β values (i.e., the weighted effect weight parameters) for the single polygenic risk score generation machine learning model are generated based at least in part on the per-model effect weight parameter set for the distinct per-model genetic variant set that is associated with the optimal genetic variant refinement model. In some embodiments, the comparatively-refined polygenic risk score generation machine learning framework comprises M polygenic risk score generation machine learning models each associated with a respective one of M genetic variant refinement models. In some of the noted embodiments: (i) each particular polygenic risk score generation machine learning model of the M polygenic risk score generation machine learning models is configured to perform operations of the equation $$MPRS = \sum_{j=1}^{N_L} X_j \beta_j,$$

where: (a) MPRS is the per-model polygenic risk score for the particular individual with respect to the target phenotype as generated by the particular polygenic risk score generation machine learning model, (b) $N_L$ is the distinct genetic variant set for the defined genetic variant refinement model that is associated with the particular polygenic risk score generation machine learning model, (c) each $x_a$ is an indicator that describes whether the genetic variant $\alpha$ in $N_L$ is present/observed in the refined GWAS data for the particular individual, and (d) each $\beta_a$, is a weighted effect weight parameter for the genetic variant in $N_L$ with respect to the target phenotype, where $\beta_a$, that is generated based at least in part on the ath value of per-model parameter numerical estimate set for the per-model parameter set that is associated with the defined genetic variant refinement model for the particular polygenic risk score generation machine learning model, and (ii) the comparatively-refined polygenic risk score generation machine learning framework is configured to generate the polygenic risk score by performing the operations of the equation $$PRS = \sum_{m=1}^{M} MPRS_m E_m,$$

where: (a) $MPRS_m$ per-model polygenic risk score for the mth polygenic risk score generation machine learning model, and (b) $E_m$ is the Bayesian evidence numerical estimate for the defined genetic variant refinement model that is associated with the mth polygenic risk score generation machine learning model.

The term "polygenic risk score" may refer to a data object that is configured to describe an estimated genomic risk score for a particular individual with respect to a target phenotype as generated by a comparatively-refined polygenic risk score generation machine learning framework. In some embodiments, when the comparatively-refined polygenic risk score generation machine learning framework includes a single polygenic risk score generation machine learning model that is associated with a respective defined genetic variant refinement model, then generating the polygenic risk score comprises: (i) for each particular genetic variant in the distinct genetic variant set for the respective genetic variant refinement model: (a) generating a genetic variant presence indicator based at least in part on whether the GWAS for the particular individual comprises the particular genetic variant, and (b) applying the per-model effect weight parameter for the particular genetic variant in the per-model effect weight parameter set for the distinct per-model genetic variant set that is associated with the respective defined genetic variant refinement model to generate a weighted genetic variant presence indicator for the particular genetic variant, and (ii) combining the weighted genetic variant presence indicators fort the genetic variants in the distinct genetic variant set for the respective genetic variant refinement model to generate the polygenic risk score. In some embodiments, when the comparatively-refined polygenic risk score generation machine learning framework includes two or more polygenic risk score generation machine learning models that is each associated with a respective defined genetic variant refinement model, then generating the polygenic risk score generation machine learning model comprises: (i) for each polygenic risk score generation machine learning model, generating a per-model polygenic risk score for the particular individual with respect to the target phenotype, and (ii) combining the per-model polygenic risk scores for the two or more polygenic risk score generation machine learning models in accordance with the Bayesian evidence numerical estimate for the defined genetic variant refinement models that are associated with the two or more polygenic risk score generation machine learning models to generate the polygenic risk score. In some embodiments, for a given polygenic risk score generation machine learning model that is associated with a respective defined genetic variant refinement model, generating the per-model polygenic risk score comprises: (i) for each particular genetic variant in the distinct genetic variant set for the respective genetic variant refinement model: (a) generating a genetic variant presence indicator based at least in part on whether the GWAS for the particular individual comprises the particular genetic variant, and (b) applying the per-model effect weight parameter for the particular genetic variant in the per-model effect weight parameter set for the distinct per-model genetic variant set that is associated with the respective defined genetic variant refinement model to generate a weighted genetic variant presence indicator for the particular genetic variant, and (ii) combining the weighted genetic variant presence indicators fort the genetic variants in the distinct genetic variant set for the respective genetic variant refinement model to generate the per-model polygenic risk score. In some embodiments, combining the per-model polygenic risk scores for the two or more polygenic risk score generation machine learning models comprises: (i) for each polygenic risk score generation machine learning model that is associated with a respective defined genetic variant refinement model, applying the Bayesian evidence numerical estimate for the respective defined genetic variant refinement model to the per-model polygenic risk score that is generated by the polygenic risk score generation machine learning model to generate a weighted per-model polygenic risk score for the polygenic risk score generation machine learning model. and (ii) combining the weighted per-model polygenic risk scores for the polygenic risk score generation machine learning models to generate the polygenic risk score.

III. Computer Program Products, Methods, and Computing Entities

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIIM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations. Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing health-related predictive data analysis. The architecture 100 includes a predictive data analysis system 101 configured to receive health-related predictive data analysis requests from external computing entities 102, process the predictive data analysis requests to generate health-related risk predictions, provide the generated health-related risk predictions to the external computing entities 102, and automatically perform prediction-based actions based at least in part on the generated polygenic risk score predictions. Examples of health-related predictions include genetic risk predictions, polygenic risk predictions, medical risk predictions, clinical risk predictions, behavioral risk predictions, and/or the like.

In some embodiments, predictive data analysis system 101 may communicate with at least one of the external computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The predictive data analysis system 101 may include a predictive data analysis computing entity 106 and a storage subsystem 108. The predictive data analysis computing entity 106 may be configured to receive health-related predictive data analysis requests from one or more external computing entities 102, process the predictive data analysis requests to generate the polygenic risk score predictions corresponding to the predictive data analysis requests, provide the generated polygenic risk score predictions to the external computing entities 102, and automatically perform prediction-based actions based at least in part on the generated polygenic risk score predictions.

The storage subsystem 108 may be configured to store input data used by the predictive data analysis computing entity 106 to perform health-related predictive data analysis as well as model definition data used by the predictive data analysis computing entity 106 to perform various health-related predictive data analysis tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Predictive Data Analysis Computing Entity

FIG. 2 provides a schematic of a predictive data analysis computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the predictive data analysis computing entity 106 may include or be in communication with one or more processing elements 205 (also referred to as processors, processing circuitry, and/or similar terms used herein interchangeably) that communicate with other elements within the predictive data analysis computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the predictive data analysis computing entity 106 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210, including but not limited to hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity—relationship model, object model, document model, semantic model, graph model, and/or the like.

In one embodiment, the predictive data analysis computing entity 106 may further include or be in communication with volatile media (also referred to as volatile storage, memory, memory storage, memory circuitry and/or similar terms used herein interchangeably). In one embodiment, the volatile storage or memory may also include one or more volatile storage or memory media 215, including but not limited to RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the predictive data analysis computing entity 106 with the assistance of the processing element 205 and operating system.

As indicated, in one embodiment, the predictive data analysis computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the predictive data analysis computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 702.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the predictive data analysis computing entity 106 may include or be in communication with one or more input elements, such as a keyboard input, a mouse input, a touch screen/display input, motion input, movement input, audio input, pointing device input, joystick input, keypad input, and/or the like. The predictive data analysis computing entity 106 may also include or be in communication with one or more output elements (not shown), such as audio output, video output, screen/display output, motion output, movement output, and/or the like.

Exemplary External Computing Entity

FIG. 3 provides an illustrative schematic representative of an external computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. External computing entities 102 can be operated by various parties. As shown in FIG. 3, the external computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the external computing entity 102 may be capable of operating with one or more air interface standards, communication protocols, modulation types, and access types. More particularly, the external computing entity 102 may operate in accordance with any of a number of wireless communication standards and protocols, such as those described above with regard to the predictive data analysis computing entity 106. In a particular embodiment, the external computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the external computing entity 102 may operate in accordance with multiple wired communication standards and protocols, such as those described above with regard to the predictive data analysis computing entity 106 via a network interface 320.

Via these communication standards and protocols, the external computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The external computing entity 102 can also download changes, add-ons, and updates, for instance, to its firmware, software (e.g., including executable instructions, applications, program modules), and operating system.

According to one embodiment, the external computing entity 102 may include location determining aspects, devices, modules, functionalities, and/or similar words used herein interchangeably. For example, the external computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the external computing entity's 102 position in connection with a variety of other systems, including cellular towers, Wi-Fi access points, and/or the like. Similarly, the external computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The external computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the external computing entity 102 to interact with and/or cause display of information/data from the predictive data analysis computing entity 106, as described herein. The user input interface can comprise any of a number of devices or interfaces allowing the external computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the external computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The external computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the external computing entity 102. As indicated, this may include a user application that is resident on the entity or accessible through a browser or other user interface for communicating with the predictive data analysis computing entity 106 and/or various other computing entities.

In another embodiment, the external computing entity 102 may include one or more components or functionality that are the same or similar to those of the predictive data analysis computing entity 106, as described in greater detail above. As will be recognized, these architectures and descriptions are provided for exemplary purposes only and are not limiting to the various embodiments.

In various embodiments, the external computing entity 102 may be embodied as an artificial intelligence (AI) computing entity, such as an Amazon Echo, Amazon Echo Dot, Amazon Show, Google Home, and/or the like. Accordingly, the external computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. Exemplary System Operations

As described below, various embodiments of the present invention describe techniques for generating a polygenic risk score generation machine learning framework that integrates an optimal genetic variant refinement model without requiring brute-force traversal of potential parameter spaces defined by various distinct genetic variant sets. In some embodiments, when a polygenic risk score for a particular individual with respect to a target phenotype is generated in accordance with the operations of the equation $$PRS = \sum_{j=1}^{N_L} X_j \beta_j$$

as described below, the genetic variant set used to generate the noted polygenic risk score generation model may be any subset of an overall set of genetic variants (e.g., the set of all single-nucleotide polymorphisms (SNPs) that are present in human genome). Selecting an optimal genetic variant set for a particular polygenic risk score generation model that is configured to generate polygenic risk scores for a particular target phenotype is a computationally challenging task. A naïve solution to this problem is to generate the optimal genetic variant set to include each genetic variant whose correlation score (e.g., p value) with respect to the target phenotype as observed by the refined GWAS data satisfies (e.g., exceeds) a defined correlation score. However, this naïve approach fails to integrate interactions between variable-size groupings of genetic variants. In contrast, various embodiments of the present invention use holistic Bayesian sampling routines to efficiently generate Bayesian evidence numerical estimates for various genetic variant refinement models and select an optimal genetic variant refinement model accordingly. This enables enhancing the accuracy of polygenic risk score generation machine learning frameworks without resorting to computationally resource-intensive traversals of potential parameter spaces defined by various distinct genetic variant sets. In doing so, various embodiments of the present invention enhance the computational efficiency of generating a polygenic risk score generation machine learning framework that integrates an optimal genetic variant refinement model in contrast to computationally-inefficient techniques that require brute-force traversal of potential parameter spaces defined by various distinct genetic variant sets.

Generating Comparatively-Refined Polygenic Risk Score Generation Models

FIG. 4 is a flowchart diagram of an example process 400 for generating a comparatively-refined polygenic risk score generation model. Via the various steps/operations of the process 400, the predictive data analysis computing entity 106 is configured to generate a comparatively-refined polygenic risk score generation machine learning framework that comprises an optimal genetic variant refinement model, where the optimal genetic variant refinement model is selected from a plurality of defined genetic variant refinement models based at least in part on Bayesian evidence numerical estimates for the plurality of defined genetic variant refinement models. Once generated, the comparatively-refined polygenic risk score generation machine learning framework can be used to generate a polygenic risk score for a particular individual with respect to a target phenotype (e.g., a target medical condition).

The process 400 begins at step/operation 401 when the predictive data analysis computing entity 106 identifies (e.g., obtains, receives, generates, and/or the like) genome-wide association studies (GWAS) data for a target phenotype (e.g., for a particular disease under conditions). In some embodiments, the GWAS data include whole-genome sequences (GWSs) for individuals that are deemed to suffer from a particular medical condition, such as from type 1 diabetes.

At step/operation 402, the predictive data analysis computing entity 106 performs quality control operations on the GWAS data to generate refined GWAS data. Examples of quality control operations include one or more of quality control operations configured to ensure that each GWS is associated with a unique subject, quality control operations configured to ensure appropriate sequencing, quality control operations configured to perform sex checks, quality control operations configured to ensure appropriate stratification of a patient cohort, and quality control operations configured to ensure that no duplicated single-nucleotide polymorphisms (SNPs) are present in the GWAS data.

At step/operation 403, the predictive data analysis computing entity 106 generates the comparatively-refined polygenic risk score generation machine learning framework based at least in part on the refined GWAS data. In some embodiments, to generate the comparatively-refined polygenic risk score generation model, the predictive data analysis computing entity 106: (i) identifies a plurality of defined genetic variant refinement models, (ii) for each defined genetic variant refinement model, samples from a per-model posterior distribution for the defined genetic variant refinement model given the refined GWAS data (or other target genome-wide association data) for the target phenotype and by using a holistic Bayesian sampling routine that is configured to generate: (a) a per-model parameter numerical estimate set for the per-model parameter set that is associated with the defined genetic variant refinement model, and (b) a Bayesian evidence numerical estimate for the defined genetic variant refinement model, and (iii) selects the optimal genetic variant refinement model as the defined genetic variant refinement model with an optimal Bayesian evidence numerical estimate as generated by the holistic Bayesian sampling routine.

In some embodiments, step/operation 403 may be performed in accordance with the process that is depicted in FIG. 5, which is an example process for generating a comparatively-refined polygenic risk score generation machine learning framework based at least in part on the refined GWAS data. The process that is depicted in FIG. 5 begins at step/operation 501 when the predictive data analysis computing entity 106 identifies (e.g., generates)M defined genetic variant refinement models.

In some embodiments, each defined genetic variant refinement model defines: (i) a distinct per-model genetic variant set, and (ii) a per-model parameter set comprising a per-model effect weight parameter set for the distinct per-model genetic variant set that is associated with the defined genetic variant refinement model. In some embodiments, a polygenic risk score is generated as a weighted sum of effect weights for genetic variants (e.g., SNPs) in a particular genetic variant set, for example in accordance with the operations of the equation $$PRS = \sum_{j=1}^{N_L} X_j \beta_j,$$

where: (i) PRS is a polygenic risk score for a particular individual with respect to a target phenotype, (ii) each $x_a$ is an indicator that describes whether the genetic variant a in a set of genetic variants $N_L$ is present/observed in the refined GWAS data for the particular individual, (iii) each $\beta_a$ is a weighted effect weight parameter for the genetic variant a in the set of genetic variants $N_L$ with respect to the target phenotype, and (iv) $N_L$ is the set of genetic variants (e.g., SNPs) that are determined/computed to be related to the target phenotype. In some embodiments, a defined genetic variant refinement model provides a recommended genetic variant set (i.e., a defined $N_L$) for the target phenotype. In some embodiments, once a defined genetic variant refinement model is identified, a proposed system may sample from a posterior distribution for the defined genetic variant refinement model to generate a Bayesian evidence numerical estimate for the defined genetic variant refinement model, and then defined genetic variant refinement model having an optimal (e.g., a maximum) Bayesian evidence numerical estimate may be selected as the optimal genetic variant refinement model.

In some embodiments, when a polygenic risk score for a particular individual with respect to a target phenotype is generated in accordance with the operations of the equation $$PRS = \sum_{j=1}^{N_L} X_j \beta_j$$

as described above, the genetic variant set used to generate the noted polygenic risk score generation model may be any subset of an overall set of genetic variants (e.g., the set of all SNPs that are present in human genome). Selecting an optimal genetic variant set for a particular polygenic risk score generation model that is configured to generate polygenic risk scores for a particular target phenotype is a computationally challenging task. A naïve solution to this problem is to generate the optimal genetic variant set to include each genetic variant whose correlation score (e.g., p value) with respect to the target phenotype as observed by the refined GWAS data satisfies (e.g., exceeds) a defined correlation score. However, this naïve approach fails to integrate interactions between variable-size groupings of genetic variants.

In some embodiments, to select an optimal genetic variant set for a particular polygenic risk score generation model, M distinct genetic variant sets (e.g., M distinct sets of SNPs, where no two SNP sets include exactly the same SNPs) are identified. Once the M distinct genetic variant sets are generated, for each genetic variant set, a posterior probability distribution $Pr(\beta, n_p, S, \ldots, |D)$ can be generated, where: (i) $\{\beta, n_p, S, \ldots\}$ is the set of parameters of the posterior probability distribution including $\beta$, which is the set of weighted effect weight parameters for each genetic in the defined the distinct genetic variant set, and (ii) D is the refined GWAS data. In some embodiments, the combination of a distinct genetic variant set and a set of parameters for a posterior probability distribution for the distinct genetic variant set is referred to herein as a defined genetic variant refinement model. Accordingly, in some embodiments, given M distinct genetic variant sets, M genetic variant refinement models are defined, with each genetic variant refinement model being associated with a respective genetic variant set and describing both the respective genetic variant set and the parameters for the posterior probability distribution that is associated with the respective genetic variant set.

As described above, in some embodiments, a defined genetic variant refinement model is associated with a per-model genetic variant set and a per-model parameter set. In some embodiments, a per-model genetic variant set is a selected set of genetic variants (e.g., SNPs) as defined by a genetic variant refinement model. In some embodiments, given V set of genetic variants, M distinct subsets of the V set of genetic variants are generated (e.g., based at least in part on subject matter expert data), and each distinct subset is adopted as the per-model genetic variant set for a respective genetic variant refinement model of M genetic variant refinement models.

In some embodiments, a per-model parameter set is a set of parameters for a posterior probability distribution for the per-model genetic variant set of a corresponding genetic variant refinement model. As described above, in some embodiments, a genetic variant refinement model is associated with a distinct genetic variant set. In some embodiments, given a particular genetic variant set, a posterior probability distribution $Pr(\beta, n_p, S, \ldots, |D)$ can be generated, where: (i) $\{\beta, n_p, S, \ldots\}$ is the set of parameters of the posterior probability distribution including $\beta$, which is the set of weighted effect weight parameters for each genetic in the defined the particular genetic variant set, and (ii) D is the refined GWAS data. In some embodiments, the combination of a genetic variant set and a set of parameters for a posterior probability distribution for the genetic variant set is referred to herein as a defined genetic variant refinement model. Accordingly, in some embodiments, given M distinct genetic variant sets, M genetic variant refinement models are defined, with each genetic variant refinement model being associated with a respective genetic variant set and describing both the respective genetic variant set and the parameters for the posterior probability distribution that is associated with the respective genetic variant set.

At step/operation 502, for each genetic variant refinement model of the M genetic variant refinement models that were identified in step/operation 501, the predictive data analysis computing entity 106 samples from the posterior probability distribution for the genetic variant refinement model given target genome-wide association data for the target phenotype and by using a holistic Bayesian sampling routine that is configured to generate: (a) a per-model parameter numerical estimate set for the per-model parameter set that is associated with the defined genetic variant refinement model, and (b) a Bayesian evidence numerical estimate for the defined genetic variant refinement model. In some embodiments, at step/operation 502, for each genetic variant refinement model of the M genetic variant refinement models that were identified in step/operation 501, the predictive data analysis computing entity 106 performs operations corresponding to a Bayesian sampling routine to sample from the posterior probability distribution for the genetic variant refinement model in order to generate both numerical estimates for the parameters of the posterior probability distribution and a numerical estimate for the Bayesian evidence term (i.e., the denominator term in a Bayesian model) that is associated with the posterior probability distribution.

In some embodiments, the sampling operations described above are performed using a holistic Bayesian sampling routine. In some embodiments, a holistic Bayesian sampling routine is configured to sample from a posterior probability distribution in a manner that traverses a parameter space by varying more than parameter dimension at each sampling iteration. Holistic Bayesian sampling routines can be contrasted with non-holistic Bayesian sampling routines such as Gibbs in which the parameter space is traversed by varying only one parameter dimension at each sampling iteration. Because of their holistic traversal approach, Holistic Bayesian sampling routines are able to capture predictive correlations between parameters more effectively. Examples of holistic Bayesian sampling routines include nested sampling routines and hybrid sampling routines that comprise a nested sampling sub-routine and a dynamic nested sampling sub-routine.

In some embodiments, when the holistic Bayesian sampling routine comprises a nested sampling sub-routine and a dynamic nested sampling sub-routine, for a particular defined genetic variant refinement model, the nested sampling sub-routine is configured to generate a first Bayesian evidence numerical estimate for the particular defined genetic variant refinement model as generated by the nested sampling sub-routine, while the dynamic nested sampling sub-routine is configured to generate a second Bayesian evidence numerical estimate for the particular defined genetic variant refinement model as generated by the dynamic nested sampling sub-routine.

In some embodiments, the Bayesian evidence numerical estimate for the particular defined genetic variant refinement model is generated based at least in part on a cross-estimate weighted combination of the first Bayesian evidence numerical estimate and the second Bayesian evidence numerical estimate, where the cross-estimate weighted combination may be generated based at least in part on (e.g., by adding) the product of applying a weight for the nested sampling routine (e.g., a weight of 0.5) to the first Bayesian evidence numerical estimate and the product of applying a weight for the dynamic nested sampling routine (e.g., a weight of 0.5) to the second Bayesian evidence numerical estimate. In some of the noted embodiments, the weight of the nested sampling routine is generated based at least in part on a historical model performance quality weight for the nested sampling routine that describes a computed accuracy of per-model polygenic risk scores generated in accordance with optimal genetic variant refinement models selected in accordance with Bayesian evidence numerical estimates that are generated using the nested sampling routine relative to ground-truth polygenic risk scores. In some of the noted embodiments, the weight of the dynamic nested sampling routine is generated based at least in part on a historical model performance quality weight for the dynamic nested sampling routine that describes a computed accuracy of per-model polygenic risk scores generated in accordance with optimal genetic variant refinement models selected in accordance with Bayesian evidence numerical estimates that are generated using the nested sampling routine relative to ground-truth polygenic risk scores.

In some embodiments, when the holistic Bayesian sampling routine comprises a nested sampling sub-routine and a dynamic nested sampling sub-routine, for a particular defined genetic variant refinement model, the nested sampling sub-routine is configured to generate a first per-model parameter numerical estimate for the per-model parameter set that is associated with the particular defined genetic variant refinement model, while the dynamic nested sampling sub-routine is configured to generate a second first per-model parameter numerical estimate for the per-model parameter set that is associated with the particular defined genetic variant refinement model. In some of the noted embodiments, for a particular defined genetic variant refinement model, if the historical model performance quality weight for the nested sampling routine exceeds the historical model performance quality weight for the dynamic nested sampling routine, then the first per-model parameter numerical estimate is adopted as the per-model parameter numerical estimate set for the per-model parameter set that is associated with the particular defined genetic variant refinement model. In some of the noted embodiments, for a particular defined genetic variant refinement model, if the historical model performance quality weight for the dynamic nested sampling routine exceeds the historical model performance quality weight for the nested sampling routine, then the second per-model parameter numerical estimate is adopted as the per-model parameter numerical estimate set for the per-model parameter set that is associated with the particular defined genetic variant refinement model.

In some embodiments, the historical model performance quality weight for the nested sampling routine is determined based at least in part on a computed accuracy of per-model polygenic risk scores generated in accordance with optimal genetic variant refinement models selected in accordance with Bayesian evidence numerical estimates that are generated using the nested sampling routine relative to ground-truth polygenic risk scores. In some embodiments, the historical model performance quality weight for the dynamic nested sampling routine is determined based at least in part on a computed accuracy of per-model polygenic risk scores generated in accordance with optimal genetic variant refinement models selected in accordance with Bayesian evidence numerical estimates that are generated using the nested sampling routine relative to ground-truth polygenic risk scores.

Accordingly, by sampling from a posterior probability distribution for a defined genetic variant refinement model in accordance with a holistic Bayesian sampling routine, the predictive data analysis computing entity 106 can not only generate numerical estimates for parameters of the posterior probability distribution, but also a numerical estimate for the Bayesian evidence term. In some embodiments, because the Bayesian evidence term is a normalization factor that describes integration of the Bayesian likelihood term across all of a prior distribution, numerically estimating the Bayesian evidence term using a non-holistic Bayesian sampling routine is challenging, while a holistic Bayesian sampling routine provides a reliable and effective estimate for this Bayesian evidence term.

In some embodiments, generating the optimal genetic variant refinement model comprises, for each defined genetic variant refinement model, sampling from a per-model posterior distribution for the defined genetic variant refinement model given target genome-wide association data for the target phenotype and by using a holistic Bayesian sampling routine that is configured to generate: (i) a per-model parameter numerical estimate set for the per-model parameter set that is associated with the defined genetic variant refinement model, and (ii) a Bayesian evidence numerical estimate for the defined genetic variant refinement model. In some embodiments, the per-model parameter numerical estimate set comprises the numerical estimates for parameters of the posterior probability distribution of a particular genetic variant refinement model as generated by the holistic Bayesian sampling routine, while the Bayesian evidence numerical estimate is the numerical estimate for the Bayesian evidence term of the posterior probability distribution of the particular genetic variant refinement model as generated by the holistic Bayesian sampling routine.

At step/operation 503, the predictive data analysis computing entity 106 generates the comparatively-refined polygenic risk score generation machine learning framework. In some embodiments, to generate the comparatively-refined polygenic risk score generation machine learning framework, the predictive data analysis computing entity 106 selecting the optimal genetic variant refinement model as the defined genetic variant refinement model with an optimal Bayesian evidence numerical estimate as generated by the holistic Bayesian sampling routine, and then generates the comparatively-refined polygenic risk score generation machine learning framework that comprises operations corresponding to applying the per-model effect weight parameter set for the distinct per-model genetic variant set that is associated with the optimal genetic variant refinement model to a per-model variant presence indicator set for the distinct per-model genetic variant set that is associated with the optimal genetic variant refinement model.

In some embodiments, a comparatively-refined polygenic risk score generation machine learning framework comprises one or more machine learning models, where the one or more machine learning models are configured to generate a polygenic risk score for a particular individual with respect to a target phenotype based at least in part on GWAS data (e.g., refined GWAS data) associated with the particular individual. In some embodiments, the comparatively-refined polygenic risk score generation machine learning framework is configured to perform operations of one or more polygenic risk score generation machine learning models, where each polygenic risk score generation machine learning model is configured to generate a polygenic risk score for a particular individual with respect to a target phenotype in accordance with the operations of the equation $$PRS = \sum_{j=1}^{N_L} X_j \beta_j,$$

where: (i) PRS is the polygenic risk score for the particular individual with respect to the target phenotype, (ii) each $x_a$ is an indicator that describes whether the genetic variant a in a set of genetic variants $N_L$ is present/observed in the refined GWAS data for the particular individual, (iii) each $\beta_a$ is a weighted effect weight parameter for the genetic variant a in the set of genetic variants $N_L$ with respect to the target phenotype, and (iv) $N_L$ is the set of genetic variants (e.g., SNPs) that are determined/computed to be related to the target phenotype. In some embodiments, the comparatively-refined polygenic risk score generation machine learning framework is configured to perform operations of a single polygenic risk score generation machine learning model, where the $N_L$ for the single polygenic risk score generation machine learning model is the distinct genetic variant set for the optimal genetic variant refinement model, and β values (i.e., the weighted effect weight parameters) for the single polygenic risk score generation machine learning model are generated based at least in part on the per-model effect weight parameter set for the distinct per-model genetic variant set that is associated with the noted optimal genetic variant refinement model.

In some embodiments, the comparatively-refined polygenic risk score generation machine learning framework comprises M polygenic risk score generation machine learning models each associated with a respective one of M genetic variant refinement models. In some of the noted embodiments: (i) each particular polygenic risk score generation machine learning model of the M polygenic risk score generation machine learning models is configured to perform operations of the equation $$ MPRS = \sum_{j=1}^{N_L} X_j \beta_j, $$

where: (a) MPRS is the per-model polygenic risk score for the particular individual with respect to the target phenotype as generated by the particular polygenic risk score generation machine learning model, (b) $N_L$ is the distinct genetic variant set for the defined genetic variant refinement model that is associated with the particular polygenic risk score generation machine learning model, (c) each $x_a$ is an indicator that describes whether the genetic variant a in $N_L$ is present/observed in the refined GWAS data for the particular individual, and (d) each $\beta_a$ is a weighted effect weight parameter for the genetic variant in $N_L$ with respect to the target phenotype, where $\beta_a$, that is generated based at least in part on the ath value of per-model parameter numerical estimate set for the per-model parameter set that is associated with the defined genetic variant refinement model for the particular polygenic risk score generation machine learning model, and (ii) the comparatively-refined polygenic risk score generation machine learning framework is configured to generate the polygenic risk score by performing the operations of the equation $$ PRS = \sum_{m=1}^{M} MPRS_m E_m, $$

where: (a) $MPRS_m$ per-model polygenic risk score for the mth polygenic risk score generation machine learning model, and (b) $E_m$ is the Bayesian evidence numerical estimate for the defined genetic variant refinement model that is associated with the mth polygenic risk score generation machine learning model. Accordingly, in some embodiments: (i) the comparatively-refined polygenic risk score generation machine learning framework further comprises a cross-model refinement model (e.g., the model that is configured to perform the operations of the equation $$ PRS = \sum_{m=1}^{M} MPRS_m E_m), $$

where the cross-model refinement model is configured to generate a cross-model weighted combination (e.g., the PRS term in the equation

26

$$ PRS = \sum_{m=1}^{M} MPRS_m E_m) $$

of each per-model polygenic risk score (e.g., each $MPRS_m$ term in the equation $$ PRS = \sum_{m=1}^{M} MPRS_m E_m), $$

for the plurality of defined genetic variant refinement models (e.g., the M defined genetic variant refinement models associated with the M polygenic risk score generation models), (ii) the cross-model weighted combination is generated based at least in part on a plurality of probabilistic model quality weights for the plurality of defined genetic variant refinement models, and (iii) each probabilistic model quality weight for a respective defined genetic variant refinement model is generated based at least in part on the Bayesian evidence numerical estimate for the respective defined genetic variant refinement model as generated by the holistic Bayesian sampling routine. In some of the noted embodiments, generating the polygenic risk score comprises adopting the cross-model weighted combination as the polygenic risk score.

At step/operation 504, the predictive data analysis computing entity 106 performs testing/validation operations on the comparatively-refined polygenic risk score generation machine learning framework using testing GWAS data. In some embodiments, if the comparatively-refined polygenic risk score generation machine learning framework satisfies one or more testing/validation objectives, the comparatively-refined polygenic risk score generation machine learning framework is adopted as the final comparatively-refined polygenic risk score generation machine learning framework that is used to generate polygenic risk scores with respect to a target phenotype.

By using the comparatively-refined polygenic risk score generation machine learning framework, various embodiments of the present invention describe techniques for generating a polygenic risk score generation machine learning framework that integrates an optimal genetic variant refinement model without requiring brute-force traversal of potential parameter spaces defined by various distinct genetic variant sets. In some embodiments, when a polygenic risk score for a particular individual with respect to a target phenotype is generated in accordance with the operations of the equation $$ PRS = \sum_{j=1}^{N_L} X_j \beta_j $$

as described above, the genetic variant set used to generate the noted polygenic risk score generation model may be any subset of an overall set of genetic variants (e.g., the set of all single-nucleotide polymorphisms (SNPs) that are present in human genome). Selecting an optimal genetic variant set for a particular polygenic risk score generation model that is configured to generate polygenic risk scores for a particular target phenotype is a computationally challenging task. A naïve solution to this problem is to generate the optimal genetic variant set to include each genetic variant whose correlation score (e.g., p value) with respect to the target phenotype as observed by the refined GWAS data satisfies (e.g., exceeds) a defined correlation score. However, this naïve approach fails to integrate interactions between variable-size groupings of genetic variants. In contrast, various embodiments of the present invention use holistic Bayesian sampling routines to efficiently generate Bayesian evidence numerical estimates for various genetic variant refinement models and select an optimal genetic variant refinement model accordingly. This enables enhancing the accuracy of polygenic risk score generation machine learning frameworks without resorting to computationally resource-intensive traversals of potential parameter spaces defined by various distinct genetic variant sets. In doing so, various embodiments of the present invention enhance the computational efficiency of generating a polygenic risk score generation machine learning framework that integrates an optimal genetic variant refinement model in contrast to computationally-inefficient techniques that require brute-force traversal of potential parameter spaces defined by various distinct genetic variant sets.

Generating Polygenic Risk Scores

FIG. 6 is a flowchart diagram of an example process 600 for generating a polygenic risk score for a particular individual with respect to a target phenotype. Via the various steps/operations of the process 600, the predictive data analysis computing entity 106 can use a comparatively-refined polygenic risk score generation machine learning framework to generate a polygenic risk score for a particular individual with respect to a target phenotype (e.g., a target medical condition).

The process that is depicted in FIG. 7 begins at step/operation 601 when the predictive data analysis computing entity 106 identifies GWAS data for the particular individual. In some embodiments, the GWAS data include the GWS for the particular individual.

At step/operation 602, the predictive data analysis computing entity 106 processes the GWAS data for the particular individual using the comparatively-refined polygenic risk score generation machine learning framework to generate the polygenic risk score for the particular individual. In some embodiments, when the comparatively-refined polygenic risk score generation machine learning framework includes a single polygenic risk score generation machine learning model that is associated with a respective defined genetic variant refinement model, then generating the polygenic risk score comprises: (i) for each particular genetic variant in the distinct genetic variant set for the respective genetic variant refinement model: (a) generating a genetic variant presence indicator based at least in part on whether the GWAS for the particular individual comprises the particular genetic variant, and (b) applying the per-model effect weight parameter for the particular genetic variant in the per-model effect weight parameter set for the distinct per-model genetic variant set that is associated with the respective defined genetic variant refinement model to generate a weighted genetic variant presence indicator for the particular genetic variant, and (ii) combining the weighted genetic variant presence indicators fort the genetic variants in the distinct genetic variant set for the respective genetic variant refinement model to generate the polygenic risk score.

In some embodiments, when the comparatively-refined polygenic risk score generation machine learning framework includes two or more polygenic risk score generation machine learning models that is each associated with a respective defined genetic variant refinement model, then generating the polygenic risk score generation machine learning model comprises: (i) for each polygenic risk score generation machine learning model, generating a per-model polygenic risk score for the particular individual with respect to the target phenotype, and (ii) combining the per-model polygenic risk scores for the two or more polygenic risk score generation machine learning models in accordance with the Bayesian evidence numerical estimate for the defined genetic variant refinement models that are associated with the two or more polygenic risk score generation machine learning models to generate the polygenic risk score.

In some embodiments, for a given polygenic risk score generation machine learning model that is associated with a respective defined genetic variant refinement model, generating the per-model polygenic risk score comprises: (i) for each particular genetic variant in the distinct genetic variant set for the respective genetic variant refinement model: (a) generating a genetic variant presence indicator based at least in part on whether the GWAS for the particular individual comprises the particular genetic variant, and (b) applying the per-model effect weight parameter for the particular genetic variant in the per-model effect weight parameter set for the distinct per-model genetic variant set that is associated with the respective defined genetic variant refinement model to generate a weighted genetic variant presence indicator for the particular genetic variant, and (ii) combining the weighted genetic variant presence indicators fort the genetic variants in the distinct genetic variant set for the respective genetic variant refinement model to generate the per-model polygenic risk score.

In some embodiments, combining the per-model polygenic risk scores for the two or more polygenic risk score generation machine learning models comprises: (i) for each polygenic risk score generation machine learning model that is associated with a respective defined genetic variant refinement model, applying the Bayesian evidence numerical estimate for the respective defined genetic variant refinement model to the per-model polygenic risk score that is generated by the polygenic risk score generation machine learning model to generate a weighted per-model polygenic risk score for the polygenic risk score generation machine learning model. and (ii) combining the weighted per-model polygenic risk scores for the polygenic risk score generation machine learning models to generate the polygenic risk score.

At step/operation 603, the predictive data analysis computing entity 106 performs one or more prediction-based actions based at least in part on the polygenic risk score. Examples of prediction-based actions including displaying a user interface that displays health-related risk predictions (e.g., at least one of epistatic polygenic risk scores, epistatic interaction scores, and base polygenic risk scores) for a target individual with respect to a set of conditions. For example, as depicted in FIG. 7, the predictive output user interface 700 depicts the health-related risk prediction for a target individual with respect to four target conditions each identified by the International Statistical Classification of Diseases and Related Health Problems (ICD) code of the noted four target conditions.

An exemplary prediction-based action includes performing operational load balancing for post-prediction systems by using polygenic-risk-score-based predictions to set the number of allowed computing entities used by the noted post-prediction systems. For example, in some embodiments, a predictive data analysis computing entity determines D inferred classifications for D individuals based at least in part on the D polygenic risk scores for the D individuals. Then, the count of individuals that are associated with an affirmative inferred classification, along with a resource utilization ratio for each individual, can be used to predict a predicted number of computing entities needed to perform post-prediction processing operations (e.g., automated investigation operations) with respect to the D individuals. For example, in some embodiments, the number of computing entities needed to perform post-prediction processing operations (e.g., automated investigation operations) with respect to D individuals can be determined based at least in part on the output of the equation:

$$R = \text{ceil}\left(\sum\nolimits_{k}^{k=K} ur_k\right),$$

where R is the predicted number of computing entities needed to perform post-prediction processing operations with respect to the D individual, ceil(.) is a ceiling function that returns the closest integer that is greater than or equal to the value provided as the input parameter of the ceiling function, k is an index variable that iterates over K individuals among the D polygenic risk scores that are associated with affirmative classifications, and $ur_k$ is the estimated resource utilization ratio for a kth individual that may be determined based at least in part on a count of utterances/tokens/words in the kth individual. In some embodiments, once R is generated, the predictive data analysis computing entity can use R to perform operational load balancing for a server system that is configured to perform post-prediction processing operations (e.g., automated investigation operations) with respect to D individuals. This may be done by allocating computing entities to the post-prediction processing operations if the number of currently-allocated computing entities is below R, and deallocating currently-allocated computing entities if the number of currently-allocated computing entities is above R.

Accordingly, as described above, various embodiments of the present invention describe techniques for generating a polygenic risk score generation machine learning framework that integrates an optimal genetic variant refinement model without requiring brute-force traversal of potential parameter spaces defined by various distinct genetic variant sets. In some embodiments, when a polygenic risk score for a particular individual with respect to a target phenotype is generated in accordance with the operations of the equation $$PRS = \sum\nolimits_{j=1}^{N_L} X_j \beta_j$$

as described above, the genetic variant set used to generate the noted polygenic risk score generation model may be any subset of an overall set of genetic variants (e.g., the set of all single-nucleotide polymorphisms (SNPs) that are present in human genome). Selecting an optimal genetic variant set for a particular polygenic risk score generation model that is configured to generate polygenic risk scores for a particular target phenotype is a computationally challenging task. A naïve solution to this problem is to generate the optimal genetic variant set to include each genetic variant whose correlation score (e.g., p value) with respect to the target phenotype as observed by the refined GWAS data satisfies (e.g., exceeds) a defined correlation score. However, this naïve approach fails to integrate interactions between variable-size groupings of genetic variants. In contrast, various embodiments of the present invention use holistic Bayesian sampling routines to efficiently generate Bayesian evidence numerical estimates for various genetic variant refinement models and select an optimal genetic variant refinement model accordingly. This enables enhancing the accuracy of polygenic risk score generation machine learning frameworks without resorting to computationally resource-intensive traversals of potential parameter spaces defined by various distinct genetic variant sets. In doing so, various embodiments of the present invention enhance the computational efficiency of generating a polygenic risk score generation machine learning framework that integrates an optimal genetic variant refinement model in contrast to computationally-inefficient techniques that require brute-force traversal of potential parameter spaces defined by various distinct genetic variant sets.

VI. Conclusion

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for generating a polygenic risk score for a target phenotype using a comparatively-refined polygenic risk score generation machine learning framework, the computer-implemented method comprising:

identifying, by one or more processors, the comparatively-refined polygenic risk score generation machine learning framework, wherein:

the comparatively-refined polygenic risk score generation machine learning framework comprises an optimal genetic variant refinement model that is selected from a plurality of defined genetic variant refinement models, each defined genetic variant refinement model: (i) is associated with: (a) a distinct per-model genetic variant set of a group of genetic variants, and (b) a per-model parameter set comprising a per-model effect weight parameter set for the distinct per-model genetic variant set of the group of genetic variants that is associated with the corresponding defined genetic variant refinement model, and (ii) is configured to generate a per-model polygenic risk score based at least in part on a per-model input feature vector corresponding to the distinct per-model genetic variant set of the group of genetic variants for the corresponding defined genetic variant refinement model and the per-model parameter set for the corresponding defined genetic variant refinement model, and generating the optimal genetic variant refinement model comprises: (i) for each defined genetic variant refinement model, sampling from a per-model posterior probability distribution for the corresponding defined genetic variant refinement model given target genome-wide association data for the target phenotype and by using a holistic Bayesian sampling routine that is configured to generate: (a) a per-model parameter numerical estimate set for the per-model parameter set that is associated with the corresponding defined genetic variant refinement model, and (b)

a Bayesian evidence numerical estimate for the corresponding defined genetic variant refinement model, and (ii) selecting the optimal genetic variant refinement model as the corresponding defined genetic variant refinement model with an optimal Bayesian evidence numerical estimate as generated by the holistic Bayesian sampling routine, generating, by the one or more processors, the polygenic risk score based at least in part on the per-model polygenic risk score for the optimal genetic variant refinement model; and performing, by the one or more processors, one or more prediction-based actions based at least in part on the polygenic risk score.

2. The computer-implemented method of claim 1, wherein the holistic Bayesian sampling routine comprises a nested sampling sub-routine.

3. The computer-implemented method of claim 1, wherein the holistic Bayesian sampling routine comprises a dynamic nested sampling sub-routine.

4. The computer-implemented method of claim 1, wherein:

the holistic Bayesian sampling routine comprises a nested sampling sub-routine and a dynamic nested sampling sub-routine, and the Bayesian evidence numerical estimate for a particular defined genetic variant refinement model is generated based at least in part on a first Bayesian evidence numerical estimate for the particular defined genetic variant refinement model as generated by the nested sampling sub-routine and a second Bayesian evidence numerical estimate for the particular defined genetic variant refinement model as generated by the dynamic nested sampling sub-routine.

5. The computer-implemented method of claim 4, wherein:

the Bayesian evidence numerical estimate for the particular defined genetic variant refinement model is generated based at least in part on a cross-estimate weighted combination of the first Bayesian evidence numerical estimate and the second Bayesian evidence numerical estimate, and the cross-estimate weighted combination is generated based at least in part on a first historical model performance quality weight for the nested sampling sub-routine and a second historical model performance quality weight for the dynamic nested sampling sub-routine.

6. The computer-implemented method of claim 1, wherein:

the comparatively-refined polygenic risk score generation machine learning framework further comprises a cross-model refinement model that is configured to generate a cross-model weighted combination of each per-model polygenic risk score for the plurality of defined genetic variant refinement models, the cross-model weighted combination is generated based at least in part on a plurality of probabilistic model quality weights for the plurality of defined genetic variant refinement models, and each probabilistic model quality weight for a respective defined genetic variant refinement model is generated based at least in part on the Bayesian evidence numerical estimate for the respective defined genetic variant refinement model as generated by the holistic Bayesian sampling routine.

7. The computer-implemented method of claim 6, wherein generating the polygenic risk score comprises:

adopting the cross-model weighted combination as the polygenic risk score.

8. A system for generating a polygenic risk score for a target phenotype using a comparatively-refined polygenic risk score generation machine learning framework, the system comprising one or more processors and one or more non-transitory computer readable media storing processor-executable instructions that, when executed by the one or more processors, cause the one or more processors to perform operations comprising:

identifying the comparatively-refined polygenic risk score generation machine learning framework, wherein:

the comparatively-refined polygenic risk score generation machine learning framework comprises an optimal genetic variant refinement model that is selected from a plurality of defined genetic variant refinement models, each defined genetic variant refinement model: (i) is associated with: (a) a distinct per-model genetic variant set of a group of genetic variants, and (b) a per-model parameter set comprising a per-model effect weight parameter set for the distinct per-model genetic variant set of the group of genetic variants that is associated with the corresponding defined genetic variant refinement model, and (ii) is configured to generate a per-model polygenic risk score based at least in part on a per-model input feature vector corresponding to the distinct per-model genetic variant set of the group of genetic variants for the corresponding defined genetic variant refinement model and the per-model parameter set for the corresponding defined genetic variant refinement model, and generating the optimal genetic variant refinement model comprises: (i) for each defined genetic variant refinement model, sampling from a per-model posterior probability distribution for the corresponding defined genetic variant refinement model given target genome-wide association data for the target phenotype and by using a holistic Bayesian sampling routine that is configured to generate: (a) a per-model parameter numerical estimate set for the per-model parameter set that is associated with the corresponding defined genetic variant refinement model, and (b) a Bayesian evidence numerical estimate for the corresponding defined genetic variant refinement model, and (ii) selecting the optimal genetic variant refinement model as the corresponding defined genetic variant refinement model with an optimal Bayesian evidence numerical estimate as generated by the holistic Bayesian sampling routine, generating the polygenic risk score based at least in part on the per-model polygenic risk score for the optimal genetic variant refinement model; and performing one or more prediction-based actions based at least in part on the polygenic risk score.

9. The system of claim 8, wherein the holistic Bayesian sampling routine comprises a nested sampling sub-routine.

10. The system of claim 8, wherein the holistic Bayesian sampling routine comprises a dynamic nested sampling sub-routine.

11. The system of claim 8, wherein:

the holistic Bayesian sampling routine comprises a nested sampling sub-routine and a dynamic nested sampling sub-routine, and the Bayesian evidence numerical estimate for a particular defined genetic variant refinement model is generated based at least in part on a first Bayesian evidence numerical estimate for the particular defined genetic variant refinement model as generated by the nested sampling sub-routine and a second Bayesian evidence numerical estimate for the particular defined genetic variant refinement model as generated by the dynamic nested sampling sub-routine.

12. The system of claim 11, wherein:

the Bayesian evidence numerical estimate for the particular defined genetic variant refinement model is generated based at least in part on a cross-estimate weighted combination of the first Bayesian evidence numerical estimate and the second Bayesian evidence numerical estimate, and the cross-estimate weighted combination is generated based at least in part on a first historical model performance quality weight for the nested sampling sub-routine and a second historical model performance quality weight for the dynamic nested sampling sub-routine.

13. The system of claim 8, wherein:

the comparatively-refined polygenic risk score generation machine learning framework further comprises a cross-model refinement model that is configured to generate a cross-model weighted combination of each per-model polygenic risk score for the plurality of defined genetic variant refinement models, the cross-model weighted combination is generated based at least in part on a plurality of probabilistic model quality weights for the plurality of defined genetic variant refinement models, and each probabilistic model quality weight for a respective defined genetic variant refinement model is generated based at least in part on the Bayesian evidence numerical estimate for the respective defined genetic variant refinement model as generated by the holistic Bayesian sampling routine.

14. The system of claim 13, wherein generating the polygenic risk score comprises:

adopting the cross-model weighted combination as the polygenic risk score.

15. One or more non-transitory computer-readable storage media for generating a polygenic risk score for a target phenotype using a comparatively-refined polygenic risk score generation machine learning framework storing instructions that, when executed by one or more processors, cause the one or more processors to perform operations comprising:

identifying the comparatively-refined polygenic risk score generation machine learning framework, wherein:

the comparatively-refined polygenic risk score generation machine learning framework comprises an optimal genetic variant refinement model that is selected from a plurality of defined genetic variant refinement models, each defined genetic variant refinement model: (i) is associated with: (a) a distinct per-model genetic variant set of a group of genetic variants, and (b) a per-model parameter set comprising a per-model effect weight parameter set for the distinct per-model genetic variant set of the group of genetic variants that is associated with the corresponding defined genetic variant refinement model, and (ii) is configured to generate a per-model polygenic risk score based at least in part on a per-model input feature vector corresponding to the distinct per-model genetic variant set of the group of genetic variants for the corresponding defined genetic variant refinement model and the per-model parameter set for the corresponding defined genetic variant refinement model, and generating the optimal genetic variant refinement model comprises: (i) for each defined genetic variant refinement model, sampling from a per-model posterior probability distribution for the corresponding defined genetic variant refinement model given target genome-wide association data for the target phenotype and by using a holistic Bayesian sampling routine that is configured to generate: (a) a per-model parameter numerical estimate set for the per-model parameter set that is associated with the corresponding defined genetic variant refinement model, and (b) a Bayesian evidence numerical estimate for the corresponding defined genetic variant refinement model, and (ii) selecting the optimal genetic variant refinement model as the corresponding defined genetic variant refinement model with an optimal Bayesian evidence numerical estimate as generated by the holistic Bayesian sampling routine, generating the polygenic risk score based at least in part on the per-model polygenic risk score for the optimal genetic variant refinement model; and performing one or more prediction-based actions based at least in part on the polygenic risk score.

16. The one or more non-transitory computer-readable storage media of claim 15, wherein the holistic Bayesian sampling routine comprises a nested sampling sub-routine.

17. The one or more non-transitory computer-readable storage media of claim 15, wherein the holistic Bayesian sampling routine comprises a dynamic nested sampling sub-routine.

18. The one or more non-transitory computer-readable storage media of claim 15, wherein:

the holistic Bayesian sampling routine comprises a nested sampling sub-routine and a dynamic nested sampling sub-routine, and the Bayesian evidence numerical estimate for a particular defined genetic variant refinement model is generated based at least in part on a first Bayesian evidence numerical estimate for the particular defined genetic variant refinement model as generated by the nested sampling sub-routine and a second Bayesian evidence numerical estimate for the particular defined genetic variant refinement model as generated by the dynamic nested sampling sub-routine.

19. The one or more non-transitory computer-readable storage media of claim 18, wherein:

the Bayesian evidence numerical estimate for the particular defined genetic variant refinement model is generated based at least in part on a cross-estimate weighted combination of the first Bayesian evidence numerical estimate and the second Bayesian evidence numerical estimate, and the cross-estimate weighted combination is generated based at least in part on a first historical model performance quality weight for the nested sampling routine and a second historical model performance quality weight for the dynamic nested sampling sub-routine.

20. The one or more non-transitory computer-readable storage media of claim 15, wherein:

the comparatively-refined polygenic risk score generation machine learning framework further comprises a cross-model refinement model that is configured to generate a cross-model weighted combination of each per-model polygenic risk score for the plurality of defined genetic variant refinement models, the cross-model weighted combination is generated based at least in part on a plurality of probabilistic model quality weights for the plurality of defined genetic variant refinement models, and each probabilistic model quality weight for a respective defined genetic variant refinement model is generated based at least in part on the Bayesian evidence numerical estimate for the respective defined genetic variant refinement model as generated by the holistic Bayesian sampling routine.

* * * * *